(12) United States Patent
Marsman (10) Patent No.: US 11,324,931 B2
(45) Date of Patent: May 10, 2022

(54) AUTONOMOUS GUIDEWIRE

(71) Applicant: Johan Willem Pieter Marsman, Hilversum (NL)

(72) Inventor: Johan Willem Pieter Marsman, Hilversum (NL)

(73) Assignee: Johan Willem Pieter Marsman, Hilversum (NL)

( * ) Notice: Subject to any disclaimer, the term of this patent is extended or adjusted under 35 U.S.C. 154(b) by 238 days.

(21) Appl. No.: 16/286,978

(22) Filed: Feb. 27, 2019

(65) Prior Publication Data

US 2019/0262589 A1   Aug. 29, 2019

(30) Foreign Application Priority Data

Feb. 27, 2018   (EP) .................................... 18158925

(51) Int. Cl.
| | |
|---|---|
| *A61M 25/09* | (2006.01) |
| *A61M 25/00* | (2006.01) |
| *A61M 25/01* | (2006.01) |
| *A61M 25/06* | (2006.01) |

(52) U.S. Cl.
CPC ........ *A61M 25/09* (2013.01); *A61M 25/0041* (2013.01); *A61M 25/0152* (2013.01); *A61M 2025/0081* (2013.01); *A61M 2025/0681* (2013.01); *A61M 2025/09083* (2013.01); *A61M 2025/09141* (2013.01); *A61M 2025/09175* (2013.01)

(58) Field of Classification Search
CPC .. A61M 2025/0081; A61M 2025/0681; A61M 2025/090833; A61M 2025/09141; A61M 2025/09175; A61M 25/0041; A61M 25/0152; A61M 25/09
See application file for complete search history.

(56) References Cited

U.S. PATENT DOCUMENTS

| | | | | |
|---|---|---|---|---|
| 3,749,086 | A | * | 7/1973 | Kline .............. A61M 25/09033 600/585 |
| 2004/0073141 | A1 | | 4/2004 | Hartley et al. |
| 2009/0209943 | A1 | * | 8/2009 | Marsman ........ A61M 25/09041 604/528 |

(Continued)

FOREIGN PATENT DOCUMENTS

| | | | |
|---|---|---|---|
| EP | 1 920 795 A1 | 5/2008 | |
| EP | 1920795 A1 * | 5/2008 | ............ A61M 31/00 |

(Continued)

OTHER PUBLICATIONS

Kevin "Chaim" Herman, MD, "Crossing the Challenging Aortic Bifurcation," Endovascular Today, pp. 45-49 (Jan. 2012).

(Continued)

*Primary Examiner* — Sean P Dougherty
*Assistant Examiner* — Alexander H Connor
(74) *Attorney, Agent, or Firm* — Leydig, Voit & Mayer, Ltd.

(57) ABSTRACT

A guidewire for guidance of a catheter or of a catheter introducer sheath into a human patient. The guidewire has, when in untensioned condition, a curved deflection section at its distal end and a shaft with one or more curved steering sections proximal of a straight section proximally neighboring the deflection section. This facilitates steering a guidewire to a predetermined location inside the patient.

16 Claims, 4 Drawing Sheets

(56) References Cited

U.S. PATENT DOCUMENTS

2011/0071503 A1* 3/2011 Takagi .............. A61M 25/0041
604/532

FOREIGN PATENT DOCUMENTS

| EP | 1 992 383 | A1 | | 11/2008 | | |
|---|---|---|---|---|---|---|
| EP | 1992383 | A1 | * | 11/2008 | ............ | A61M 25/09 |
| EP | 2 740 513 | A1 | | 6/2014 | | |
| EP | 1920795 | B1 | * | 2/2016 | ............ | A61M 25/01 |
| EP | 1992383 | B1 | * | 4/2020 | ............ | A61M 25/09 |
| WO | WO 00/53250 | A1 | | 9/2000 | | |
| WO | WO 01/17601 | A1 | | 3/2001 | | |
| WO | WO 2004/018031 | A2 | | 3/2004 | | |
| WO | WO 2008/013441 | A1 | | 1/2008 | | |
| WO | WO-2010110132 | A1 | * | 9/2010 | ...... | A61M 25/09041 |

OTHER PUBLICATIONS

Mukesh Tripathi, MD, Mnams et al., "Direction of the J-Tip of the Guidewire, in Seldinger Technique, Is a Significant Factor in Midplacement of Subclavian Vein Catheter: A Randomized, Controlled Study," International Anesthesia Research Society, Anesth Analg 2005; 100:21-4, pp. 21-24 (2005).

European Patent Office, European Search Report in corresponding European Application No. 18158925.0, dated Aug. 10, 2018 (11 pages).

* cited by examiner

AUTONOMOUS GUIDEWIRE

CROSS-REFERENCE TO RELATED APPLICATIONS

This application claims priority to European Application No. 18158925.0, filed Feb. 27, 2018, the contents of which are expressly incorporated by reference in their entirety, including any references contained therein.

BACKGROUND OF THE INVENTION

The present invention relates to a guidewire. A guidewire is a device that is used in a number of different medical procedures to guide an implement, such as a vascular catheter, a catheter-mounted heart valve, an aortic endograft, an endotracheal tube or a gastric feeding tube, into a patient towards a desired position within the patient. Guidewires are used in a number of diagnostic and interventional fields, such as diagnostic and interventional cardiology, diagnostic and interventional neuroradiology, diagnostic and interventional radiology, urology, gastroenterology, vascular surgery, minimally invasive vascular interventions such as angioplasty, stenting, thrombolysis, transcatheter aortic valve insertion (TAVI), and endovascular abdominal aortic aneurysm repair (EVAR).

In vascular uses, a physician is required to navigate the guidewire through the vasculature of the patient. This is done in order to position the distal end of the guidewire at a desired location. In the text, the distal end of the guidewire is the end that is to enter the patient's body. The proximal end of the guidewire is not inserted into the patient's body. The shaft of the guidewire is the section in between its proximal and distal end. Generally, the shaft is only partly inserted into the body and a part of the shaft that is not in the body is in the hands of the physician.

In other uses, a physician is required to navigate the guidewire through hollow organs, such as the urinary tract, the gastro-intestinal tract, and the bile ducts. This is done in order to position the distal end of the guidewire at a desired location. Then a diagnostic or therapeutic catheter is fed over the guidewire to the desired location for the planned intervention (e.g. dilating or stenting a narrowed duct).

The distal end of the guidewire generally has a curved deflection section at its distal end to cause the guidewire to move in a desired direction when advanced into the patient at a bifurcation or in a particularly curved vessel. The deflection section may be curved with a small radius to provide an angled tip which is oriented at an angle relative to the shaft. The shaft and the proximal end of the guidewire are straight. Positioning the distal end of the guidewire at the desired location can be tough and time consuming due to complex vascular anatomy and due to abnormalities of the vessel lumen caused by vascular disease.

The physician manipulates the distal end of the guidewire through the vasculature of the patient to the desired location by pinching and torqueing the shaft of the guidewire with his fingers.

Because the positioning and steering of the distal end of the guidewire is performed under fluoroscopic guidance, a difficult and time consuming positioning procedure brings about a relatively long screening time and therefore an increased procedural radiation exposure dose imposed to the patient.

Many efforts have been made to facilitate navigating of a guidewire tip to a location within a patient. For instance EP 1 920 795 A1 discloses medical apparatuses, in particular stylets, for insertion into a body cavity, which have a plurality of curved sections. The curved sections are curved in different planes that intersect each other. The angle between these planes corresponds to the angle between planes in which corresponding curves of lumen in the patient's body are curved, so that the stylet can spontaneously assume a position in which the curved sections are located in corresponding curves of lumen in the patient's body and the apparatus does not have to be steered.

EP 1 992 383 A1 discloses a guidewire with three successive curves second and third curves being curved in opposite directions than the first and, respectively, second curves, making it difficult to erroneously enter into a side branch in a blood vessel.

SUMMARY OF THE INVENTION

It is an object of the invention to facilitate steering a guidewire with a curved deflection section at its distal end to a predetermined location inside a patient.

According to the invention, this object is achieved by providing a guidewire for guidance of a catheter or of a catheter introducer sheath into a human patient, the guidewire, when in untensioned condition, having:

at its distal end, a rounded tip having a radius larger than a guidewire circumference radius or a floppy tip section having more flexibility than a proximally adjacent section of the guidewire; and a curved deflection section closely proximal of the tip and extending over an angle of curvature such that the tip is spaced from a continuation of an axis of a shaft section proximal of the curved deflection section, wherein:

the shaft section has a curved steering section proximal of a straight section proximally neighboring the deflection section;

the straight section proximally neighboring the deflection section is of a length of 2-80 cm; and the deflection section and the curved steering section of the shaft are curved in mutually parallel planes.

The invention can also be embodied in a kit of:

a guidewire for guidance of a catheter or of a catheter introducer sheath into a human patient, the guidewire, when in untensioned condition, having:

at its distal end, a rounded tip having a radius larger than a guidewire circumference radius or a floppy tip section having more flexibility than a proximally adjacent section of the guidewire; and a curved deflection section closely proximal of the tip and extending over an angle of curvature such that the tip is spaced from a continuation of an axis of a shaft section proximal of the curved deflection section, wherein:

the shaft section has a curved steering section proximal of a straight section proximally neighboring the deflection section; and the deflection section and the curved steering section of the shaft are curved in mutually parallel planes; and a needle dimensioned such that the guidewire can extend through the needle with the curved deflection section projecting distally from the needle, i.e. inside the patient's body, and the curved steering section being located proximally from the needle, i.e. outside the patient's body.

The invention can further be embodied in a method for steering a guidewire for guidance of a catheter or of a catheter introducer sheath into a human patient, the guidewire, when in untensioned condition, having:

at its distal end, a rounded tip having a radius larger than a guidewire circumference radius or a floppy tip section having more flexibility than a proximally adjacent section of the guidewire; and a curved deflection section closely proximal of the tip and extending over an angle of curvature such that the tip is spaced from a continuation of an axis of a shaft section proximal of the curved deflection section, wherein:

the shaft section has a curved steering section proximal of a straight section proximally neighboring the deflection section; and the deflection section and the curved steering section of the shaft are curved in mutually parallel planes;

wherein the guidewire extends through a needle, the catheter or the catheter introducer sheath into the patient's body, the curved deflection section projects distally from the needle, the catheter or the catheter introducer sheath and the curved steering section is located at least partially proximally from the needle, the catheter or the catheter introducer sheath and outside the patient's body; and wherein the deflection section is steered by exerting, outside of the patient, a normal force on a portion of the curved steering section or a more proximal portion of the guidewire.

Conventional guidewires are supplied with a straight shaft and a physician steers a distal end of a guidewire to a desired location by pinching and torqueing the shaft with his fingers. The function of the shaft is transmitting rotational and longitudinal (axial) forces exerted by the physician onto the shaft of the guidewire to the distal end of the guidewire. In contrast to conventional guidewires, in the present invention the shaft of the guidewire is not straight over its entire length, but has one or more curved steering sections thereby providing the shaft, besides with the conventional function, with additional functions that facilitate the physician steering the guidewire to a predetermined location inside the patient's body by exerting a normal force on the guidewire section projecting proximally outside the patient's body.

For instance according to the invention, the curvature (i.e. the deviation from being straight) of a portion of the shaft of the guidewire allows the rotational orientation of the distal end of the guidewire to be controlled in a particularly simple and accurate manner. If a lateral force (i.e. a force with a directional component normal to a longitudinal direction in which the guidewire is orientated where the lateral force is exerted) is exerted on the curved steering section of the shaft portion of the guidewire or a lateral reaction force is caused to be exerted on the curved steering section of the shaft portion of the guidewire, the curved steering section is urged to rotate to a position accommodating the exerted force, thereby causing the deflection section to be rotated to a position oriented in a direction determined by the orientation in which the deflection section is curved relative to the direction in which the curved steering section of the shaft portion of the guidewire is curved. So, if the curved steering section of the shaft of the guidewire projects proximally from a needle or an introducer sheath outside the patient's body, exerting a transverse force on a portion of the guidewire proximally from the curved steering section of the shaft, or on a proximal portion of the curved steering section of the shaft itself, causes the guidewire to rotate until the curvature of the curved steering section of the shaft is oriented in the direction in which the transverse force is exerted. This causes the curvature of the distal curved deflection section inside the patient's body to be rotated accordingly, so that a steering effect is achieved. If the curvature of the distal curved deflection section and the curvature of the curved steering section are in parallel planes, which may be in a single common plane, the direction of deflection of the curvature of the curved steering section outside the patient's body is parallel to the direction of deflection of the curvature of the curved deflection section inside the patient's body, which is particularly helpful when navigating the guidewire tip into a desired branching inside the patient's body. The deflection of the steering section and of the deflection section may be in a common direction or in mutually opposite directions.

The bent shaft of the guidewire allows the physician to securely control the rotational orientation of the distal end of the guidewire and to steer the distal end of the guidewire to a desired direction, not by rotating the guidewire about its central axis where it is held, but by moving the proximal end of the guidewire like moving a tiller or a joystick so that its curvature is caused to be curved in a direction that is associated to the desired direction of deflection of the distal end of the guidewire.

If the curvature of the distal curved deflection section and the curvature of the curved steering section are in parallel planes, which parallel planes may be in a single common plane, the distal curved deflection section can be caused to deflect in a direction into which the curved steering section is rotated if the curved steering section and the distal curved deflection section are curved in the same direction or, the distal curved deflection section can be caused to deflect in a direction opposite to the direction into which the curved steering section is rotated if the curved steering section and the distal curved deflection section are curved in opposite directions.

Thus, the invention provides the physician a superior and reliable manual control of the guidewire and the direction of its distal tip, while simultaneously providing the physician with visible and tactile feedback about the actual rotational direction of the distal tip of the guidewire.

The steering functionality is enhanced if the guidewire has a core wire of a shape memory alloy such as Nickel Titanium (also known as Nitinol or NiTi). Nickel Titanium shows super elastic transformation upon stress and strain and has specific temperature ranges for shape memory transformation. These properties allow the steering curvature of the guidewire in untensioned condition to be made in a simple manner.

The various straight and curved segments of the guidewire may have different core wire thicknesses. Also, the degrees of shape memory of the various curves may differ. Distal curves that will enter the patient's body may for instance be less stiff than proximal curves that will remain outside the patient's body.

Further advantages, features and details of the present invention will be elucidated on the basis of a description of one or more embodiments with reference to the accompanying drawings.

DETAILED DESCRIPTION OF THE DRAWINGS

Figure 1:
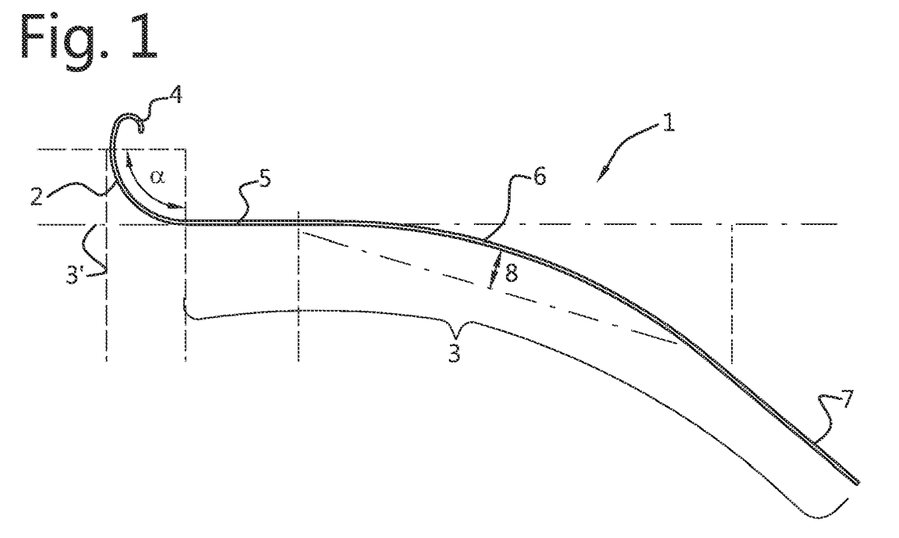
FIG. 1 is a schematic side view of a first example of a guidewire according to the present invention.

FIGS. 1-4 show a first example of a guidewire 1 according to the invention. In FIG. 1, the guidewire is shown in untensioned condition, i.e. in a condition not subjected to loads elastically deforming the guidewire 1. In this condition, the guidewire 1 has, at its distal end, a rounded tip 4 having a radius larger than a guidewire circumference radius. In this example, the rounded tip 4 includes a curved, hook-shaped section, forming a hook that is open in a direction generally towards and along a directly adjacent section of the guidewire 1 proximally of the rounded tip 4. Instead or additionally, the tip 4 may be a floppy tip section having more flexibility than a proximally adjacent section of the guidewire. The guidewire 1 further has a curved deflection section 2 closely proximal of the tip 4 and extending over an angle of curvature t such that the tip 4 is spaced from a continuation 3' of an axis of a shaft section 3 proximal of the curved deflection section 2. The deflection section 2 is curved in the same direction as the curvature of the rounded tip 4 and has an angle of curvature smaller than that of curvature forming the rounded tip 4.

Generally, the rounded tip section 4 may for instance have a radius of 1-4 mm. The curved deflection section 2 may for instance extend over an angle of 45-165°, have a radius of 5-30 mm and/or be located at a distance of less than 5-15 mm from a proximal end of the tip 4 or located directly adjacent to a proximal end of the tip.

Figure 3:
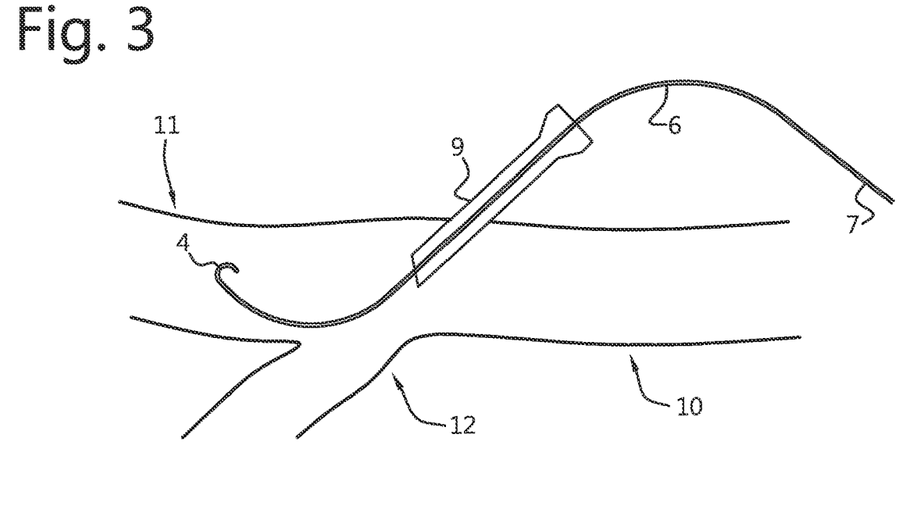
FIG. 3 is a schematic side view of the guidewire of FIG. 1 in a vascular situation wherein a tip of a distal end of the guidewire is oriented upwards.
Figure 4:
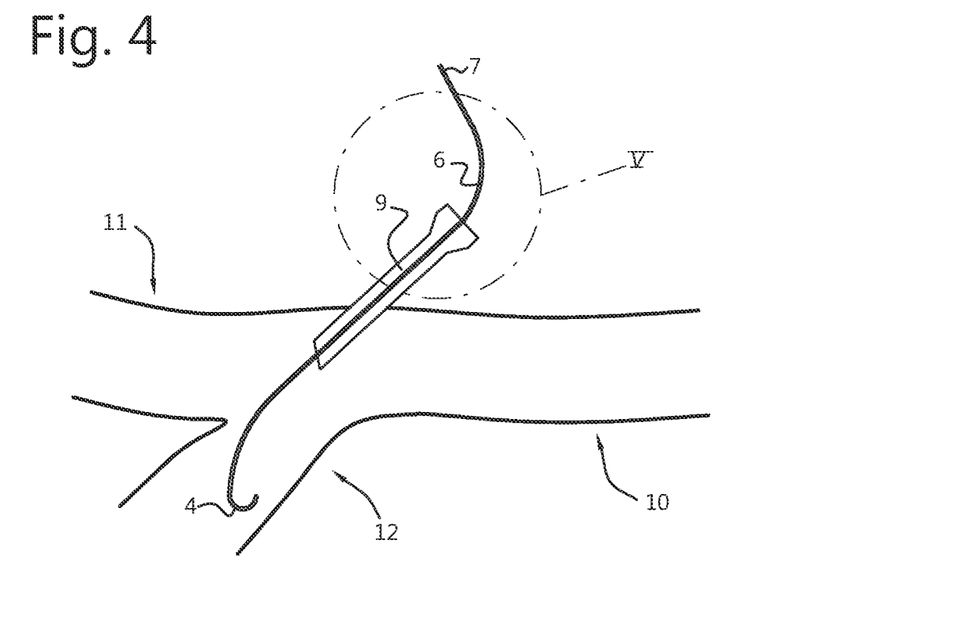
FIG. 4 is a schematic side view of the guidewire of FIG. 1 in a vascular situation wherein the desired direction of the tip of the distal end of the guidewire is oriented downwards.
Figure 5:
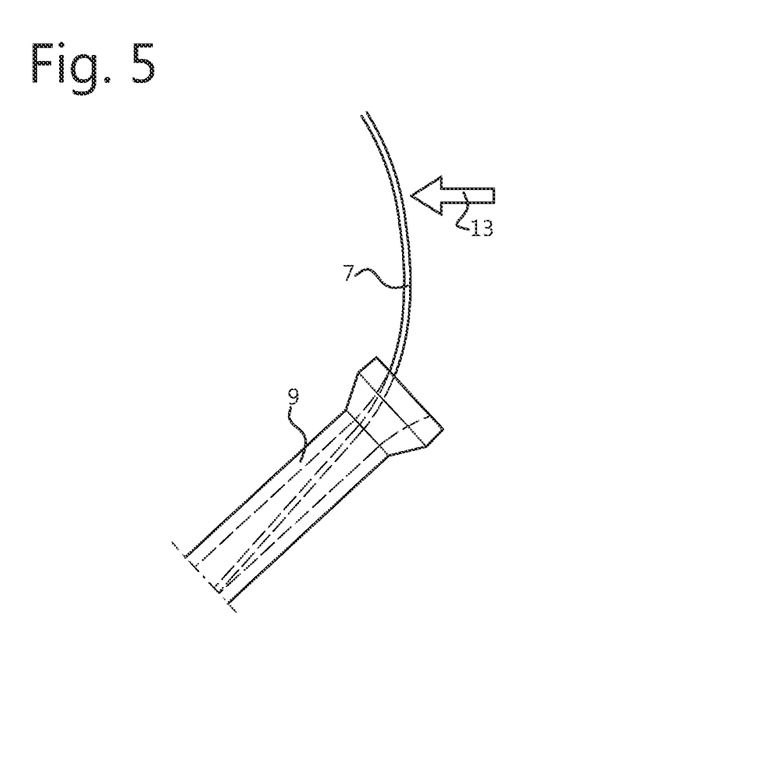
FIG. 5 is an enlarged view of a portion V of FIG. 4.

The shaft section 3 has a curved steering section 6 proximal of a straight section 5 proximally neighboring the deflection section 2 and a further straight section 7 proximally of the curved steering section 6. In FIGS. 3-5, the guidewire 1 is shown in a position introduced through a needle 9 into a blood vessel 10 which bifurcates into an upper branch 11 and a lower branch 12. In the human body this vascular configuration occurs e.g. in the groin, where the Common Femoral Artery bifurcates into the Superficial Femoral Artery and the Profunda Femoral Artery.

In this example, the curvature of the curved steering section 6 of the shaft 3 is oriented such that the curvature has an inside facing into a direction of curvature opposite to a deflection direction in which the deflection section 2 deflects from the continuation 3' of the axis of the shaft section 3. Also, the inside of the curvature of the curved steering section 6 of the shaft 3 is facing into the same direction as the inside of the curvature of the tip end 4 of the guidewire 1.

FIGS. 3-5 illustrate that if a normal force is exerted onto a portion of the shaft 3 of the guidewire 1, the shaft portion 3 is urged to rotate into a position in which the curvature of the curved steering section 6 is curved essentially in a direction in which the normal force is exerted, i.e. such that the rotational position of the curvature accommodates to the direction into which it is urged. In FIG. 3, the normal forces are predominantly exerted on the curved steering section 6 and the proximal straight section 7 of the shaft section 3 of the guidewire 1 due to gravity and cause the tip 4 of the guidewire 1 to be steered into the upper branch 11 of the blood vessel 10. FIGS. 4 and 5 illustrate the effect of exerting a normal force 13 generally opposite to the forces exerted by gravity (see FIG. 5). This causes the deflection section 2 to turn downwardly, so that the tip 4 is deflected and steered into the lower branch 12 of the blood vessel 10.

If, as is most usual in clinical practice, it is desired to steer the tip 4 into the Superficial Femoral Artery (in FIG. 3 represented by the upper branch 11 of the blood vessel 10), the guidewire 1 can simply be left to assume a rotational position of the distal end imposed by gravity force unto the proximal straight section 7 as shown in FIG. 3, so that ensuring that the guidewire 1 enters the Superficial Femoral Artery requires only little steering effort by the physician. In clinical practice this means that the physician does not have to pinch and rotate the shaft of the guidewire in order to direct the tip end 4 of the guidewire 1 from the Common Femoral Artery (in FIG. 3 represented by the blood vessel 10) into the Superficial Femoral Artery (in FIG. 3 represented by the upper branch 11 of the blood vessel 10), but that the guidewire 1 almost steers itself into the Superficial Femoral Artery and that little steering effort has to be made by the physician.

For this clinical use, the length of the shaft 3 may for instance be at least 30, 40 or 50 cm and at most 65 or 100 cm, e.g. 45 or 65 cm and the length of the curved steering section 6 of the shaft 3 may for instance be (in order of increasing preference) 5-65 cm, 11-60 cm, or 20-55 cm, e.g. 40 cm, to achieve a sufficiently strong steering effect over a sufficiently large range of insertion depths at which the tip is likely to approach the bifurcation of the Common Femoral Artery at which steering in the right direction is required.

For easy handling of the guidewire, in the untensioned condition, the steering section 6 preferably has a larger radius of curvature than the deflection section 2, the radius of curvature of the steering section 6 being preferably at least two, three or four times as large as the radius of curvature of the deflection section.

The length of the distal straight section 5 may for instance be 2-6 cm or 3-5 cm, e.g. 4 cm, so that the tip 4 of the guidewire 1 is near the bifurcation when the steering effect of the curved steering section is most pronounced. To allow for steering over a larger range of insertion depths, the length of the distal straight section 5, which transfers steering action from the curved steering section 6 to the curved deflection section 2, is preferably larger than 6 cm or, in order of increasing preference, at least 7, 9, 11 or 13 cm. For ease of handling and directness of steering, the length of the distal straight section 5 is preferably not more than 55 cm or, in order of increasing preference, not more than 40, 35, 25 or 20 cm.

The length of the proximal straight section 7 may for instance be 2-8 cm, e.g. 4 cm to provide a straight proximal end. For increased versatility and catheter exchange the length of the proximal straight section 7 is preferably at least 6 cm or, in order of increasing preference, at least 10, 25 or 50 cm. For ease of handling the length of the proximal straight section 7 is preferably not more than 55 cm or, in order of increasing preference, not more than 40, 35, 25 or 20 cm.

The deflection section 2 of the guidewire 1 may for instance be curved as described in WO2008/013441. The largest distance 8 of the curved steering section 6 of the shaft 3 from a straight line between ends of the curve may for instance measure be 5-60 mm or 10-40 mm, e.g. 30 mm and the angle of curvature between opposite ends of the curved steering section 6 may for instance be 15-45° or 20-40°, e.g. 30° to achieve a steering effect of sufficient magnitude without affecting functionality of the guidewire 1 after the curved steering section 6 has partially or completely been inserted into the patient.

Figure 2:
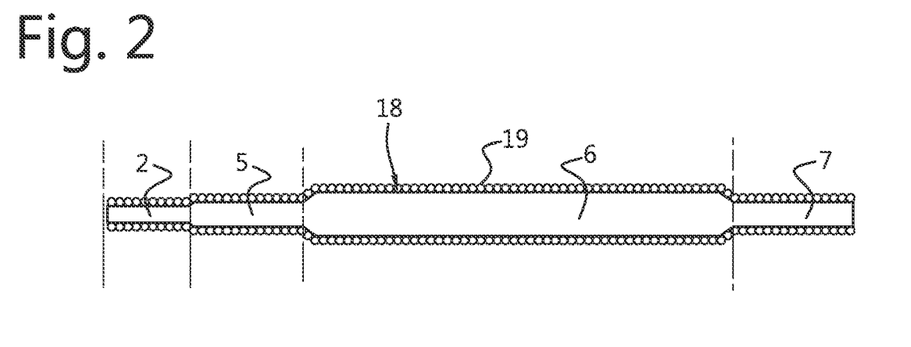
FIG. 2 is a schematic sagittal cross-sectional view of a core wire and a spring wire extending helically around the core wire of the guidewire of FIG. 1.

In this example, the guidewire 1 has a core wire 18 and a spring wire (not shown) extending helically around the core wire 18 as is common in prior art guidewires. FIG. 2 shows, by way of example, relative thicknesses of the core wire 18 in the various segments 2, 5, 6, and 7 of the guidewire 1. If the relative thickness of the curved steering section 6 is taken to be 100%, the relative thickness of the proximal and distal straight sections 5 and 7 may for instance be 60-90%, e.g. 75%, and the relative thickness of the distal end 2 of the guidewire 1 may for instance be 30-60%, e.g. 50%. Thus, the curved steering section 6 is relatively stiff, so that a small deflection provided by the curved steering section 6 is sufficient for direct and precise steering of the distal sections 2 and 4. The core wire 18 is preferably of a shape memory alloy such as Nickel Titanium (also known as Nitinol or NiTi).

Generally, a thicker core wire is stiffer than a thinner one. In the deflection section 2 and the tip end 4 of the guidewire 1, the core wire has the smallest thickness, so that this section is the most elastic section and is very adaptable to the shape of the vessel lumen it is inserted into. The deflection section 2 should be flexible enough to prevent any harm that could be exerted by the tip end 4 of the guidewire 1.

In the present example, the core wire of the curved steering section 6 of the shaft section 3 has the greatest thickness, which makes this section the most stiff section and stiff enough to impose a direction of curvature of the curved steering section 6, even if the steering section 6 in unloaded condition would curve upwardly in proximal direction away from the needle 9. Thus, gravity causes the guidewire 1 to rotate particularly reliably if the guidewire is released and the curvature of the curved steering section 6 is urged downwards by gravity. In turn, this rotation causes the tip end 4 of the guidewire 1 to turn to an upwardly deflected orientation and advancing the guidewire then results in the tip section 4 to enter the upper branch 11 of the blood vessel 10 as shown in FIG. 3.

The core wires of proximal and distal straight sections 5 and 7 of the guidewire 1 according to the present example have an intermediate thickness. Consequently, the stiffness of the distal straight section 5 is intermediate, which is advantageous to accurately transmit the rotational orientation of the curved steering section 6 to the curved deflection section 2 of the guidewire 1. The stiffness of the proximal straight section 7 of the guidewire 1 according to the present example is also intermediate, which is advantageous for easy insertion of the proximal end of the guidewire into a port of a catheter or the like that is to be guided over the guidewire to a desired intravascular location.

Figure 6:
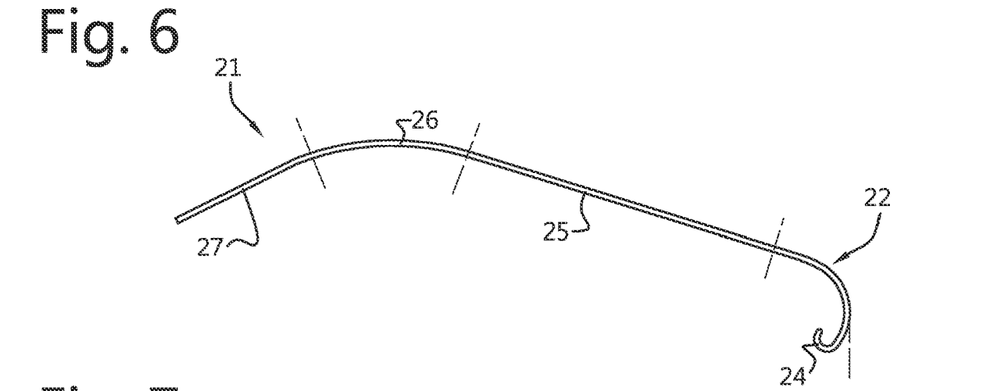
FIG. 6 is a schematic side view of a second example of a guidewire according to the present invention.

FIG. 6 shows a side view of another example of a guidewire 21 according to the invention. The guidewire 21 has a curved deflection section 22 and a shaft section 23. The deflection section 22 of the guidewire 21 has a tip end 24. The shaft section 23 of the guidewire 21 has a proximal straight section 25, a distal straight section 27, and a curved steering section 26 in between. The curvature of the curved steering section 26 of the shaft 23 is curved in the same plane and into the same direction as the curvature of the curved deflection section 22 of the guidewire 21.

The length of the shaft section 23 may be for instance 100-230 cm e.g. 160 cm and the length of the curved steering section 26 of the shaft 23 may for instance be 5-65 cm or 20-55 cm, e.g. 40 cm. The length of the proximal straight section 27 may for instance be 65-110 cm e.g. 85 cm and the length of the distal straight section 25 may for instance be 15-80 cm or 30-55 cm, e.g. 35 cm. The deflection section 22 of the guidewire 1 may for instance be curved as described in WO2008/013441. The largest distance 28 of the curved steering section 26 of the shaft section 23 from a straight line between ends of the curved steering section 26 may for instance measure 5-35 mm or 10-30 mm e.g. 15 mm.

Figure 7:
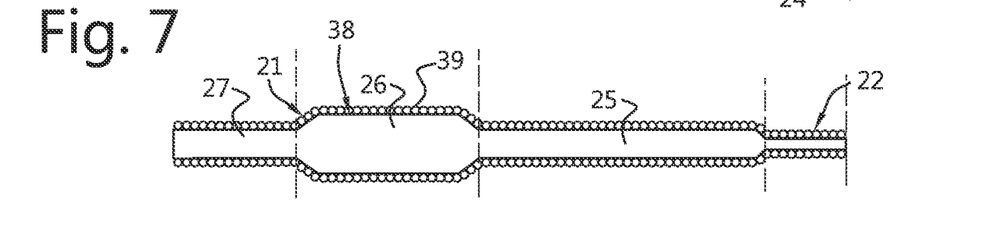
FIG. 7 is a schematic sagittal cross-sectional view of a core wire and a spring wire extending helically around the core wire of the guidewire of FIG. 6.

The guidewire 21 has a core wire 38 and a spring wire (not shown). FIG. 7 schematically shows the relative thicknesses of the core wire 38 in the various segments of the guidewire 21, which may be as in the previous example.

Figure 8:
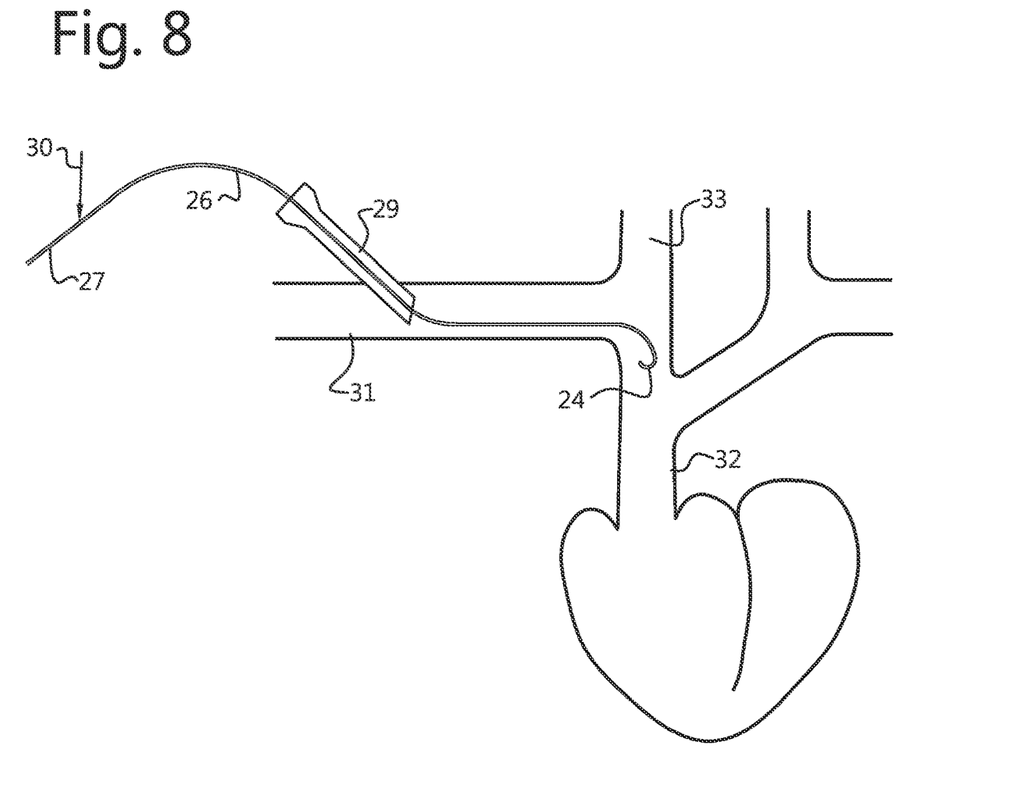
FIG. 8 is a schematic top view of a vascular situation and a guidewire according to FIGS. 6 and 7 being advanced therein.

FIG. 8 shows the guidewire 21 in a position introduced through a needle 29 into a vascular configuration that schematically represents a vascular configuration in a human thorax (seen in front view). In analogy to thoracic anatomy the needle 29 has been introduced into a right Subclavian Vein 31. Due to a transverse force 30, exerted downwards (as seen in the drawing) on the proximal straight section 27 of the shaft section 23 of the guidewire 21, the curvature of the deflection section 22 and accordingly the tip 24 of the guidewire is directed downwards into the direction of a Superior Vena Cava 32. Concurrently the tip 24 of the guidewire is deflected away from the entrance of a left Internal Jugular Vein 33. In clinical practice, in the work-up of placement of a central venous catheter, it is important that a guidewire is pointing downwards to a Superior Vena Cava because the desired position of the central venous catheter that is fed over the guidewire is in the Superior Vena Cava. However, misplacement of the central venous catheter in an ipsilateral Internal Jugular Vein is a common complication. See "Direction of the J-tip of the guidewire, in Seldinger technique, is a significant factor in misplacement of Subclavian Vein catheter: a randomized, controlled study" by Mukesh Tripathi in Anesthesia Analgesia, 2005, volume 100, p. 21. FIG. 8 illustrates that the curved steering section 26 of the guidewire 21 allows the physician to steer the distal tip 24 of the guidewire away from the right Internal Jugular Vein 33, not by rotating the guidewire about its central axis, but by moving the proximal section 27 downwards by exerting the transverse force 30 and thus preventing the complication of misplacement of the central venous catheter in the right Internal Jugular Vein.

Figure 9:
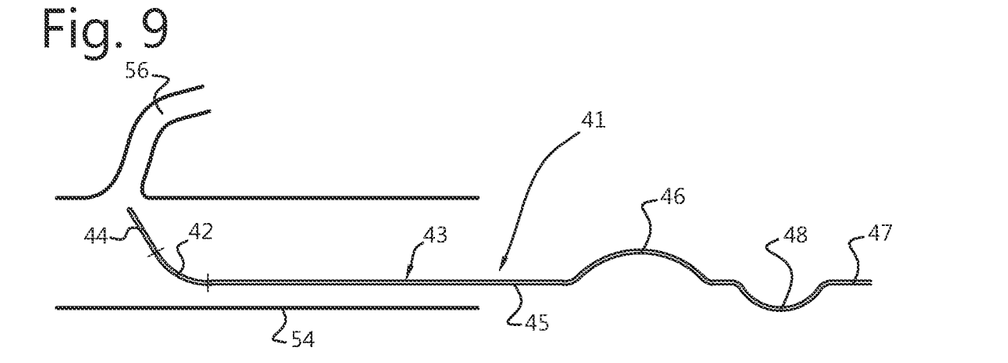
FIG. 9 is a schematic side view of a third example of a guidewire according to the present invention in a vascular situation.
Figure 10:
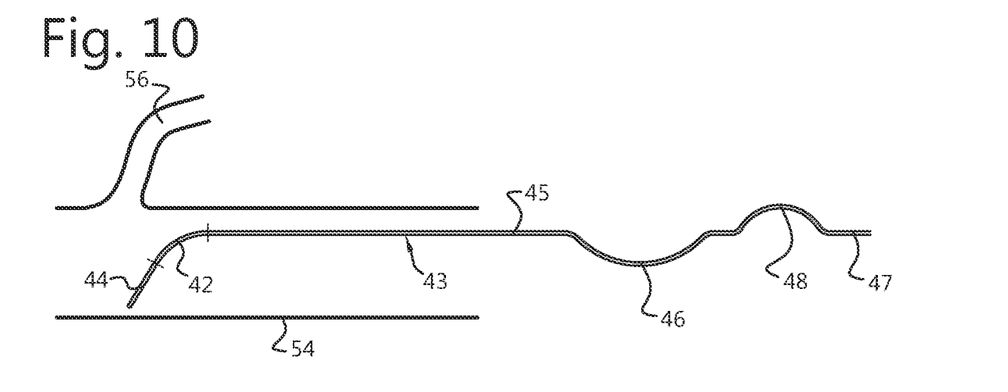
FIG. 10 is a schematic side view of the guidewire of FIG. 9 turned upside down.

FIGS. 9 and 10 provide side views of a further example of a guidewire 41 according to the invention. This guidewire 41 has an angled distal end 44 projecting distally from a curved deflection section 42 distally of a shaft section 43. The shaft section 43 has, from its proximal end to its distal end, a proximal straight shaft section 47, a proximal curved steering section 48, a distal curved steering section 46 and a distal straight shaft section 45. The curvature of the distal curved steering section 46 is curved into the same direction as the direction into which the angled distal end 44 is angled, while the curvature of the distal curved steering section 48 is curved in a direction opposite of the direction into which the angled distal end 44 is angled.

In FIG. 9, the guidewire 41 is schematically shown in a position in an Aorta 54 with the angled distal end 44 pointing forwards in the direction of the origin of a Superficial Mesenteric Artery 56. In FIG. 10 the guidewire 41 is axially in the same position, but rotated such that the angled distal end 44 points away from the origin of the Superficial Mesenteric Artery 56.

One function of the oppositely curved steering sections 46 and 48 of the shaft section 43 is enhancement of grip on the guidewire 41 by the fingers of the physician so that the curved steering sections 46, 48 of the shaft 43 can be operated as a steering crank. This improves the ability of the physician to manipulate the angled distal end 44 of the guidewire 41 through the vasculature of a patient.

Figure 11:
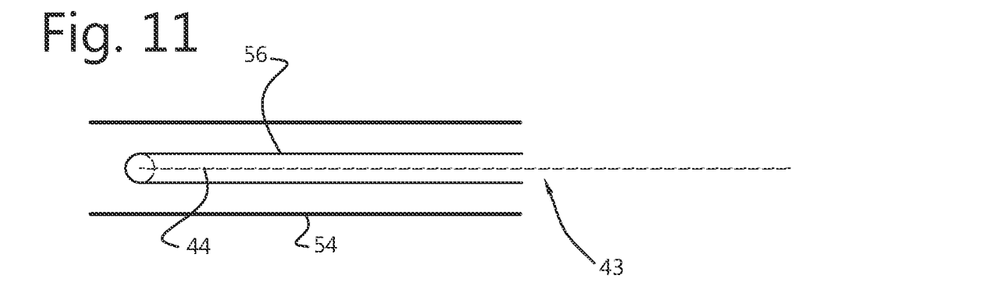
FIG. 11 is a top view of the situation shown in FIG. 9 or of the situation shown in FIG. 10.

Another function of the curved steering sections 46 and 48 is to continuously indicate to the physician in a tactile manner via his or her hand and visually in which direction the angled distal end 44 of the guidewire 41 is pointing (and heading if the guidewire 41 is advanced). Knowing the direction of deflection of the angled distal end 44 is particularly important when the physician is fluoroscopically viewing an X-ray image of the patient being treated, obtained from X-rays oriented backwards or forwards about perpendicular to the patient's longitudinal body axis during steering of the guidewire 41 into the Superficial Mesenteric Artery 56. As illustrated by FIG. 11, in such a situation, the fluoroscopic image is the same regardless whether the angled distal end 44 points forwards into the direction of the origin of the Superficial Mesenteric Artery 56, as depicted in FIG. 9, or points away from the origin of the Superficial Mesenteric Artery 56, as depicted in FIG. 10. In contrast to the fluoroscopic image giving no information whether the distal end 44 of the guidewire 41 is pointing forwards or backwards, the physician gets such information from the orientation of the distal curved steering section 46 which orientation can continuously be felt by the hand and seen with a brief glance. Consequently, the physician can reliably steer the angled distal end 44 into the Superficial Mesenteric Artery 56 by feeling and turning the convexity of the distal curved steering section 46 forwards, as depicted in FIG. 9. Because the positioning and steering of a distal end of a guidewire into a Superficial Mesenteric Artery is performed under fluoroscopic guidance, application of a guidewire 41 results in a decreased procedural radiation exposure dose imposed to the patient.

Figure 12:
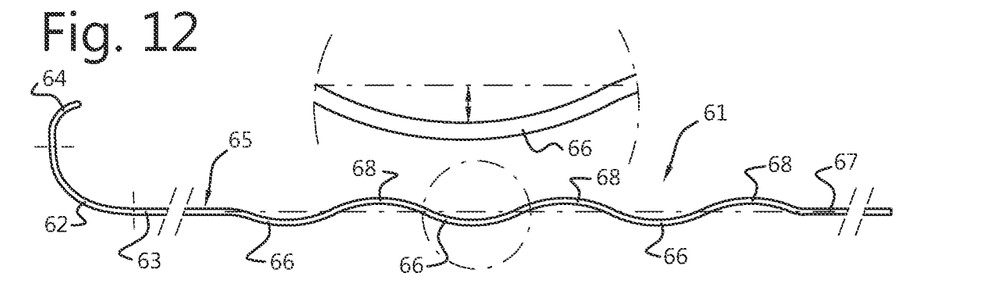
FIG. 12 is a schematic side view of a fourth example of a guidewire according to the invention.

FIG. 12 shows a further example of a guidewire 61 according to the invention. This guidewire 61 has an angled distal end 64 projecting distally from a curved deflection section 62 distally of a shaft section 63. The shaft section 63 has, from its proximal end to its distal end, a proximal straight shaft section 67, three pairs of steering sections 66, 68, the curved steering sections of each pair being curved in mutually opposite directions, and a distal straight shaft section 65.

Since a plurality pairs of oppositely curved steering section 66, 68 is provided, the effect of enhanced grip on the guidewire 61 by the fingers of the physician, accordingly improvement of the ability of the physician to manipulate the angled distal end 64 of the guidewire 61 through the vasculature of a patient, is provided along a longer length of the shaft 63 of the guidewire 61 than is provided by a single pair of oppositely curved steering sections. This is particularly advantageous in clinical applications in which navigation is difficult at widely varying insertion depths.

The present invention is described in the foregoing on the basis of several preferred embodiments. Depending on contemplated applications, different aspects of different embodiments can be combined. This includes all combinations which can be made by a skilled person on the basis of this document. These preferred embodiments are not limitative for the scope of protection of this document. The rights sought are defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventor expects skilled artisans to employ such variations as appropriate, and the inventor intends for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A guidewire for guidance of a catheter or of a catheter introducer sheath into a human patient, wherein the guidewire, when in an untensioned condition, has:
   at a distal end, a tip that is either a rounded tip section having a radius of curvature larger than a radius of a circumference of the guidewire or a floppy tip section having more flexibility than a proximally adjacent section of the guidewire; and a curved deflection section proximal of the tip section, at a distance of less than 15 mm from a proximal end of the tip section or located directly adjacent to the proximal end of the tip section, wherein the curved deflection section extends over an angle of curvature such that the tip is spaced from a continuation of an axis of a shaft section proximal of the curved deflection section, wherein:
  the shaft section has a curved steering section proximal of a straight section proximally neighboring the curved deflection section;
  the straight section, proximally neighboring the curved deflection section, is of a length of 2-80 cm;
  the curved deflection section and the curved steering section of the shaft are curved in mutually parallel planes, and
  the curved steering section has a length of 5-65 cm.

2. The guidewire according to claim 1, wherein the curved steering section is longer than the curved deflection section.

3. The guidewire according to claim 1, wherein, in the untensioned condition, the curved steering section has a larger radius of curvature than a radius of curvature of the curved deflection section.

4. The guidewire of claim 3 wherein the larger radius of curvature of the curved steering section is at least twice as large as the radius of curvature of said deflection section.

5. The guidewire according to claim 1, wherein, in the untensioned condition, the curved steering section is curved over an angle of deflection, from a straight line, of 15-45°.

6. The guidewire according to claim 1, wherein, in the untensioned condition, the curved steering section forms a curve having a largest distance to a straight line between ends of the curve of 5-60 mm.

7. The guidewire according to claim 1, wherein the shaft section has a straight portion proximally of the curved steering section.

8. The guidewire according to claim 1, further having a further curved steering section, wherein:
  a first one, of the curved steering section and the further curved steering section, has a curvature curved in a first direction,
  a second one, of the curved steering section and the further curved steering section, has a curvature curved in a second direction, and
  the first direction differs from said second direction.

9. The guidewire according to claim 8, comprising a plurality of pairs of the first steering section and second steering section having oppositely curved curvatures, the first steering section and the second steering section alternating in an array of the pairs of first and second steering sections.

10. The guidewire of claim 8 wherein the first direction is opposite to the second direction.

11. The guidewire according to claim 1, further having a core wire of a shape memory alloy and a spring wire extending helically around the core wire.

12. The guidewire according to claim 1, having a core wire having a first thickness in the curved deflection section and a second thickness in the shaft section, and the second thickness is larger than the first thickness.

13. The guidewire according to claim 12, wherein in the curved steering section of the shaft section, the core wire has a larger thickness than a thickness of the core wire in at least a straight section of the shaft section that is proximal or distal of the curved steering section.

14. The guidewire according to claim 1, wherein the curved deflection section and the curved steering section of the shaft section are curved in a common sense of curvature.

15. A kit comprising:
  a guidewire for guidance of a catheter or of a catheter introducer sheath into a human patient, wherein the guidewire, when in an untensioned condition, has:
    at a distal end, a tip that is either a rounded tip section having a radius of curvature larger than a radius of a circumference of the guidewire or a floppy tip section having more flexibility than a proximally adjacent section of the guidewire;
    a curved deflection section proximal of the tip section, at a distance of less than 15 mm from a proximal end of the tip section or located directly adjacent to the proximal end of the tip section, wherein the curved deflection section extends over an angle of curvature such that the tip is spaced from a continuation of an axis of a shaft section proximal of the curved deflection section, wherein:
      the shaft section has a curved steering section proximal of a straight section proximally neighboring the curved deflection section;
      the straight section, proximally neighboring the curved deflection section, is of a length of 2-80 cm; and
      the curved deflection section and the curved steering section of the shaft are curved in mutually parallel planes; and
  a needle,
  wherein the needle and the guidewire are arranged for bringing the guidewire in a position extending through the needle with the curved deflection section projecting distally from the needle and the curved steering section being located proximally from the needle, and
  wherein the curved steering section has a length of 5-65 cm.

16. A method for steering a guidewire extending through a needle, a catheter or a catheter introducer sheath into a human patient, wherein the guidewire, when in an untensioned condition, has:
  at a distal end, a tip that is either a rounded tip section having a radius of curvature larger than a radius of a circumference of the guidewire or a floppy tip section having more flexibility than a proximally adjacent section of the guidewire; and
  a curved deflection section proximal of the tip section, at a distance of less than 15 mm from a proximal end of the tip section or located directly adjacent to the proximal end of the tip section, wherein the curved deflection section extends over an angle of curvature such that the tip is spaced from a continuation of an axis of a shaft section proximal of the curved deflection section, wherein:
    the shaft section has a curved steering section proximal of a straight section proximally neighboring the curved deflection section;
    the straight section, proximally neighboring the curved deflection section, is of a length of 2-80 cm; and
    the curved deflection section and the curved steering section of the shaft are curved in mutually parallel planes,
  wherein the curved deflection section projects distally from the needle,
  wherein the catheter or the catheter introducer sheath and the curved steering section is located at least partially proximally from the needle, the catheter or the catheter introducer sheath and outside of the patient; and wherein the curved deflection section is steered by exerting, outside of the patient, a normal force on a portion of the curved steering section or a more proximal portion of the guidewire, and wherein the normal force urges the curved steering section to rotate to a position accommodating to the exerted force, thereby exerting a torque causing the guidewire to rotate so that the deflection section is rotated to a position oriented in a direction determined by the orientation in which the deflection section is curved relative to the direction in which the curved steering section of the shaft portion of the guidewire is curved.

* * * * *